(12) United States Patent
Rao et al.

(10) Patent No.: US 9,232,901 B2
(45) Date of Patent: Jan. 12, 2016

(54) APPARATUS AND METHOD FOR AUTOMATICALLY IDENTIFYING FETAL HEART RATE BASELINE (75) Inventors: Jian Rao, Shenzhen (CN); Yonghua Zeng, Shenzhen (CN); Dewei Chen, Shenzhen (CN); Wusun Chen, Shenzhen (CN)

(73) Assignee: EDAN INSTRUMENTS, INC., Shenzhen (CN)

( * ) Notice: Subject to any disclaimer, the term of this patent is extended or adjusted under 35 U.S.C. 154(b) by 212 days.

(21) Appl. No.: 14/009,507

(22) PCT Filed: Jul. 7, 2011

(86) PCT No.: PCT/CN2011/076947
§ 371 (c)(1),
(2), (4) Date: Oct. 2, 2013

(87) PCT Pub. No.: WO2013/000179
PCT Pub. Date: Jan. 3, 2013

(65) Prior Publication Data
US 2014/0031707 A1    Jan. 30, 2014

(30) Foreign Application Priority Data

Jun. 29, 2011    (CN) .......................... 2011 1 0178033

(51) Int. Cl.
A61B 5/04      (2006.01)
A61B 5/024     (2006.01)
A61B 5/00      (2006.01)
A61B 8/08      (2006.01)

(52) U.S. Cl.
CPC .............. *A61B 5/02411* (2013.01); *A61B 5/725* (2013.01); *A61B 5/7253* (2013.01); *A61B 8/0866* (2013.01); *A61B 8/5223* (2013.01)

(58) Field of Classification Search
CPC ........... A61B 5/02405; A61B 5/02411; A61B 5/725; A61B 5/7253
See application file for complete search history.

(56) References Cited

U.S. PATENT DOCUMENTS

2009/0054797 A1*  2/2009  Miller et al. ................... 600/511
2010/0137727 A1*  6/2010  Sameni et al. ................ 600/511

* cited by examiner

*Primary Examiner* — Michael Kahelin
*Assistant Examiner* — Mallika D Fairchild
(74) *Attorney, Agent, or Firm* — Symbus Law Group, LLC; Clifford D. Hyra (57) ABSTRACT An apparatus and method for automatically identifying FHR baseline includes collecting FHR data within a preset duration to obtain an FHR data sequence h'(n); preprocessing the collected FHR data sequence h'(n) to obtain a corresponding FHR data sequence during the preprocessing; selecting a primary dominant peak value according to the frequency distribution of the corresponding FHR data sequence during the preprocessing; and identifying a dynamic baseline according to the corresponding FHR data sequence and the primary dominant peak value during the preprocessing to obtain the dynamic baseline, and display and print the dynamic baseline. The apparatus and method effectively prevents the impact caused by regular change of the FHR to the baseline solution, and accurately reflects the FHR baseline and changes thereof of a fetus under different conditions.

12 Claims, 6 Drawing Sheets

APPARATUS AND METHOD FOR AUTOMATICALLY IDENTIFYING FETAL HEART RATE BASELINE

This application claims the benefit of Chinese patent application No. 201110178033.1, filed Jun. 29, 2011, which is hereby incorporated by reference in its entirety.

FIELD OF THE INVENTION

The present invention relates to the field of bio-medical signal processing, and more particularly relates to an apparatus and method for automatically identifying FHR baseline.

BACKGROUND OF THE INVENTION

FHR baseline is not only an important indicator which reflects the development state of a fetal central nervous system and indicates fetal safety, but also a middle parameter which shall firstly be determined by the medical staff when they analyze fetal monitoring (hereinafter referred to as fetal monitoring) diagram. Generally, the FHR baseline will gradually decrease with increasing gestational weeks, and the normal range is 110 bpm~160 bpm. The medical staff shall attach importance to too high FHR baseline or too low FHR baseline. They shall find out the cause of the abnormality immediately, determine whether this exception has clinical significance, and provide the basis for the intervention measures. For example, during pregnancy, if the FHR baseline drops and is below 100 bpm, they shall consider that there may be congenital heart disease. However, during childbirth, FHR baseline abnormalities are warning signs of fetal distress. At this time, they shall find out the reason for the exception as soon as possible and take certain intervention measures to eliminate the abnormalities, thus ensuring safety of the fetus. Meanwhile, the FHR baseline is also the basis for the medical staff to determine other fetal intermediate physiological parameters, such as acceleration, deceleration, mutation, etc. These intermediate parameters may be determined only on the basis of the determination of the FHR baseline.

Currently, a clinical method for calculating the FHR baseline is mainly an average method. Effective FHR data of 10 minutes or more is obtained through a fetal monitoring module. After the data are processed simply, their average values are calculated. Furthermore, a straight line is drawn on a fetal monitoring drawing based on the average values and taken as the FHR baseline. However, this method is only suitable for conditions where the FHR-curve is relatively stable and there is no change in FHR baseline. Actually, due to fetal movement, uterine contractions and the impacts of various external stimuli, the FHR is accelerated and decelerated as well as has other regular changes. As the average method may not avoid the impact on the calculation results caused by these changes, the calculated FHR baseline is always deviated from actual values. Meanwhile, as the FHR baseline may vary with the changes of fetal wake cycle, as to the average method, only one value may be obtained from all of the data, and hence the changes of the FHR baseline may not be identified. Therefore, if the fetus is under different states, the FHR baseline may vary. As the FHR baseline identification method in the prior art not only cannot avoid the impact on the results caused by the FHR regular changes but also cannot vary with the different states of the fetus, the calculated FHR baseline deviates from the actual values, and regular changes of the FHR cannot be displayed in fetal monitoring diagrams. In a word, as the average method cannot process the interference data, the calculated FHR baseline is inaccurate and unstable.

DISCLOSURE OF THE INVENTION

Technical Problems

The objective of the invention is to overcome the shortcomings of bad correction and variability in identifying an FHR baseline in the prior art, provide an apparatus and method for automatically identifying an FHR baseline, obtain the dynamic baseline, and facilitate the FHR baseline to have corresponding changes according to different fetal states.

Technical Solutions

The objective of the invention is realized through the following technical proposals:

The invention relates to an apparatus for automatically identifying FHR baseline, mainly comprising:

a FHR data collecting module, a FHR data preprocessing module, a primary dominant peak value selecting module, a dynamic baseline identifying module and a main control module, wherein the FHR data collecting module is connected with the main control module, is used for collecting the FHR data within the preset duration, further obtains FHR data sequence $h'(n)$, and transmits the FHR data sequence $h'(n)$ to the main control module;

the FHR data preprocessing module is connected with the main control module, is used for carrying out data transfer, error data processing, effective data rate comparison, average filtering and interpolation processing for the FHR data sequence $h'(n)$ transmitted by the main control module, obtains the preprocessed FHR data sequence $B(m)$, and transmits the corresponding results obtained during preprocessing to the main control module;

the primary dominant peak value selecting module is connected with the main control module, is used for carrying out frequency transferring, distribution sequencing and primary dominant peak value judging for the corresponding results obtained during preprocessing that the main control module has transmitted, and transmits the results to the main control module;

the dynamic baseline identifying module is connected with the main control module, is used for working out the filtering start point T according to the preprocessed FHR data sequence $B(m)$ and a primary dominant peak value transmitted by the main control module, carries out the lowpass filtering and data recovery for the sequence $B(m)$ to further obtain the dynamic FHR baseline, and transmits the results to the main control module; and the main control module is connected with the FHR data collecting module, the FHR data preprocessing module, the primary dominant peak value selecting module, the dynamic baseline identifying module and a displaying/printing module, and used for controlling the operation of the FHR data collecting module, the FHR data preprocessing module, the primary dominant peak value selecting module, the dynamic baseline identifying module and the displaying/printing module.

As the further technical proposal of the invention, the automatically identifying FHR baseline apparatus also comprises a fetal heart signal collecting processing transferring module, a collecting duration judging module, a parameter-preset module and the displaying/printing module;

the fetal heart signal collecting processing transferring module is connected with the FHR data collecting module and used for collecting the fetal heart signals received from an ultrasonic probe, transferring the signals into the FHR data and transmitting the signals to the FHR data collecting module;

the collecting duration judging module is connected with the FHR data collecting module and used for judging whether the collecting time exceeds the preset duration; if the collecting time exceeds the preset duration, timeout signals are transmitted to the FHR data collecting module;

the parameter preset module is connected with the collecting duration judging module, the FHR data preprocessing module, the primary dominant peak value selecting module and the dynamic baseline identifying module, and used for pre-setting the parameters of each module; and the displaying/printing module is connected with the main control module and used for identifying the results according to the dynamic baseline transmitted by the main control module, displaying the FHR baseline on a fetal monitoring drawing, and printing it.

As the further technical proposal of the invention, the FHR data preprocessing module further comprises:

a data transfer unit used for transferring the FHR data sequence h'(n) collected by the FHR data collecting module and obtaining new FHR value sequence H(n) taking a pulse interval as a unit;

an error data processing unit used for carrying out error data processing for the FHR value sequence H(n) according to a preset signal quality judging standard and obtaining an effective FHR data sequence V(n);

a comparing unit used for calculating an effective data rate L of a fetal heart according to the sequences V(n) and H(n) and judging whether it is larger than a preset threshold U, wherein if L is larger than the preset threshold U, the data continue to be preprocessed; otherwise, the data stop being preprocessed and new FHR data are collected again;

an average filtering unit used for carrying out the average filtering processing for the effective FHR data sequence V(n) and hence obtaining the sequence A(m) while establishing a position mapping relation of the two sequences V(n) and A(m); and an interpolation processing unit used for fitting an invalid data part in the sequence A(m) with a linear interpolation method and hence obtaining the sequence B(m).

As the further technical proposal of the invention, the main dominant peak value module further comprises:

a frequency distribution unit used for working out each FHR frequency of the effective FHR data sequence V(n) and hence obtaining a frequency distribution sequence p'(k);

a sequencing unit used for sequencing the sequence p'(k) according to the order from small to large of the FHR values and hence obtaining the distribution sequence P(k);

a primary dominant peak value judging unit used for judging whether there is a frequency value in the sequence P(k) larger than I previous frequency values and larger than J latter frequency values, wherein if there is the frequency value, the FHR value corresponding to the frequency value is taken as the primary dominant peak value; if there is not the primary dominant peak value, the FHR value corresponding to the maximum frequency is selected to be taken as the primary dominant peak value; if there is the primary dominant peak value, it is traversed; the FHR value, corresponding to the primary frequency value of which the swept area is S times larger than the total frequency distribution area, is taken as the primary dominant peak value, wherein I, J and S are preset parameters.

As the further technical proposal of the invention, the dynamic baseline identifying module further comprises:

a filtering start-point obtaining unit used for working out the filtering start point T according to the primary dominant peak value, and selecting the value in K previous points in the sequence B(m), wherein the distance between the value and the primary dominant peak value does not exceed threshold Q; and the value is the closest to the primary dominant peak value; the value is just the filtering start point T, wherein K and Q are preset parameters.

a lowpass filtering unit used for processing the sequence B(m) with the lowpass filtering according to the filtering start point T and hence obtaining a pre-dynamic baseline sequence B1(m); and a baseline recovery unit used for carrying out the data recovery for the pre-dynamic baseline sequence with a copy method according to the mapping relation f and hence obtaining a dynamic baseline sequence B3(n).

As the further technical proposal of the invention, the dynamic baseline identifying module further comprises:

a baseline checking unit used for checking the pre-dynamic baseline sequence B1(m) obtained through the lowpass filtering unit and hence obtaining the pre-dynamic baseline sequence B2(m); the pre-dynamic baseline sequence B2(m) obtains the dynamic baseline sequence through the baseline recovery unit.

The invention relates to a method for automatically identifying FHR baseline, mainly comprising:

Step 1: collecting FHR data within a preset duration to obtain an FHR data sequence h'(n);

Step 2: preprocessing the collected FHR data sequence h'(n) to obtain a corresponding FHR data sequence during preprocessing;

Step 3: selecting a primary dominant peak value according to the frequency distribution of the corresponding FHR data sequence during preprocessing;

Step 4: working out a filtering start point according to the primary dominant peak value, carrying out lowpass filtering and data recovery for the corresponding FHR data sequence during preprocessing according to the filtering start point, and further obtaining a dynamic FHR baseline.

As the further technical proposal of the invention, before the Step 1, the method also comprises collecting fetal heart signals received from an ultrasonic probe and transferring the fetal heart signals into the FHR data; after Step 4, the method also comprises displaying and printing dynamic FHR baseline.

As the further technical proposal of the invention, the Step 2 comprises:

Step 21: transferring the FHR data sequence h'(n) and obtaining new FHR value sequence H(n) taking a pulse interval as a unit;

Step 22: carrying out error data processing for the FHR value sequence H(n) according to a preset signal quality judging standard and obtaining an effective FHR data sequence V(n);

Step 23: calculating an effective data rate L of a fetal heart according to the sequences V(n) and H(n) and judging whether it is larger than a preset threshold U; if L is larger than the preset threshold U, the data continue to be preprocessed; otherwise, the data stop being preprocessed and return to the Step 1 again to collect new FHR data;

Step 24: if the L is larger than the preset threshold U, the average filtering processing is carried out with the effective FHR data sequence V(n) to obtain the sequence A(m) while establishing a position mapping relation f of the two sequences V(n) and A(m);

Step 25: fitting an invalid data part in the sequence A(m) with a linear interpolation method and hence obtaining the sequence B(m).

As the further technical proposal of the invention, the Step 3 comprises:

Step 31: working out each FHR frequency for the corresponding FHR data sequence (i.e. the effective FHR data sequence V(n)) during preprocessing to obtain frequency distribution p'(k);

Step 32: sequencing the sequence p'(k) according to the order from small to large of the FHR values and hence obtaining the distribution sequence P(k);

Step 33: judging whether there is a frequency value in the sequence P(k) larger than I previous frequency values and larger than J latter frequency values, wherein if there is such a frequency value, the FHR value corresponding to the frequency value is taken as the primary dominant peak value; if there is no primary dominant peak value, the FHR value corresponding to the maximum frequency is selected to be taken as the primary dominant peak value; if there is the primary dominant peak value, it is traversed; the FHR value, corresponding to the primary frequency value of which the swept area is S times larger than the total frequency distribution area, is taken as the primary dominant peak value, wherein I, J and S are preset parameters.

As the further technical proposal of the invention, the Step 4 comprises:

Step 41: working out the filtering start point T according to the primary dominant peak value, and selecting the value from K previous points in the sequence B(m), wherein the distance between the value and the primary dominant peak value does not exceed threshold Q and the value is the closest to the primary dominant peak value, the value is just the filtering start point T, wherein K and Q are preset parameters.

Step 42: carrying out the lowpass filtering for the sequence B(m) and the filtering start point T and judging each value in the sequence B(m) before the filtering, wherein if the absolute difference between the value and the primary dominant peak value exceeds threshold M, the filtering is not carried out with the value; otherwise, the lowpass filtering is carried out to obtain the pre-dynamic baseline sequence B1(m), wherein M is a preset parameter;

Step 43: carrying out the data recovery for the pre-dynamic baseline sequence with a copy method according to the mapping relation f and hence obtaining a dynamic baseline sequence B3(n).

As the further technical proposal of the invention, the Step 42 further comprises: firstly, the forward direction of the sequence B(m) passes through a lowpass filter and hence obtains the sequence B0(m); secondly, the reverse direction of the sequence B0(m) passes through the lowpass filter and hence obtains the preset baseline sequence B1(m).

As further technical proposal of the invention, the invention further comprises the following steps between the Step 42 and Step 43:

checking the sequence B1(m), correcting the sequence B1(m) and B(m) to obtain the sequence C(m), and calculating number N continuously larger than zero in the sequence C(m), wherein if the N is larger than threshold R, the positions of N data in the sequence C(m) are marked; similarly, the positions in the sequence C(m), where the number continuously smaller than zero exceeds the threshold R, are marked; the marked positions correspond to the data in the sequence B(m); the data on the position are replaced with the sequence B(m); meanwhile, these positions, corresponding to the positions in the sequence V(n), are worked out according to the mapping relation f; the data of the corresponding position in the sequence V(n) are replaced with the corresponding data in the sequence V(n) in Step 3; and then Step 3 and Steps 41 and 42 of Step 4 are implemented again; the data on these positions in the sequence B1(m) are replaced with the obtained sequence, thus obtaining the pre-dynamic baseline sequence B2(m), wherein if the abovementioned steps do not result in marked positions, the pre-dynamic baseline sequence B2(m) is the sequence B1(m), wherein R is a preset parameter.

Beneficial Effects

The technical proposal provided in the invention is based on an automatically identifying dynamic baseline method of lowpass filtering and may effectively filter interference data in FHR data, and avoid the impact on baseline solution caused by FHR regular changes. The proposal is suitable for not only sleep period of a fetus whose FHR baseline does not change but also wake or restlessness period of the fetus whose FHR baseline may change. The baseline level and the changes thereof of the fetus may be reflected accurately when the fetus is under different states.

BRIEF DESCRIPTION OF THE DRAWINGS

For easy description, the invention is illustrated by the following preferred embodiments and the accompanying drawings in detail.

DETAILED DESCRIPTION OF THE PREFERRED EMBODIMENTS

In order to make clearer the objective and technical proposal of the invention, with the combination of the drawings and embodiments, the invention shall be further described in more details. It shall be understood that the embodiments described here are only used for describing the invention but are not used for limiting the invention.

Figure 1:
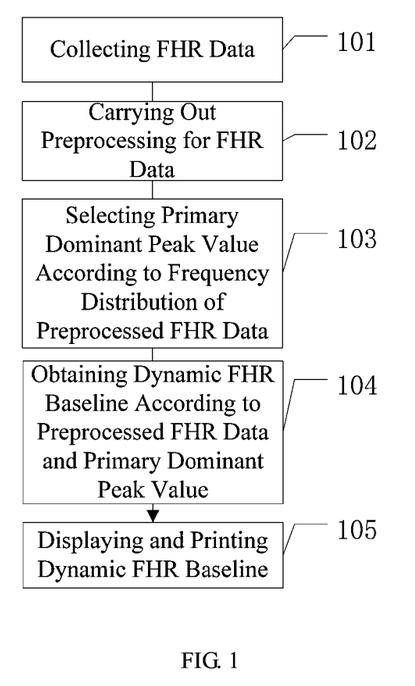
FIG. 1 is a flow chart of one embodiment of an automatically identifying FHR dynamic baseline method according to the invention.
Figure 5:
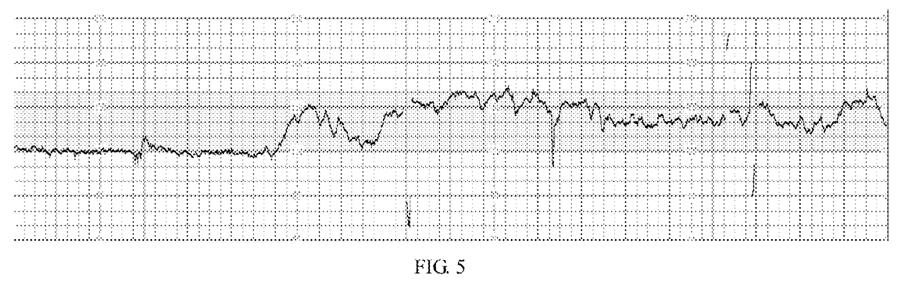
FIG. 5 is FHR data collected originally.

In order to realize the technical proposal of the automatically identifying FHR dynamic baseline, the invention mainly comprises an upper computer and a low computer. The lower computer mainly obtains the FHR signals through an ultrasonic probe, then the hardware filtering, processing and autocorrelation algorithm are carried out on the FHR signals to calculate the FHR. The upper computer is mainly used for receiving the data from the lower computer, displays and stores the FHR data, draws the FHR curve, and identifies, displays and prints FHR data processing and dynamic baseline. The flow of a main processing method is shown as FIG. 1:

101. collecting the FHR data within the preset duration;

The upper computer collects n-minute FHR data and obtains the FHR data sequence h'(n). FIG. 5 is original FHR data collected by the upper computer, wherein in the embodiment at least ten-minute data are needed to be collected. According to Fetal Electronic Monitoring, generally, it needs at least ten-minute FHR data to determine the FHR baseline.

102. preprocessing the collected FHR data;

Data transferring, error data processing, effective data rate comparison, average filtering and interpolation processing are successively carried out on the FHR data sequence to obtain the FHR data sequence corresponding to different preprocessing processes.

103. selecting the primary dominant peak value according to the frequency distribution of the processed FHR data;

As to the effective FHR data sequence obtained through the preprocessing step, frequency is transferred, distribution and sequencing are carried out, and the primary dominant peak value is judged to further select the primary dominant peak value.

104. obtaining the dynamic FHR baseline according to the preprocessed FHR data and the primary dominant peak value;

The filtering start point is worked out according to the primary dominant peak value. Lowpass filtering is carried out according to the filtering start point and the preprocessed FHR data to obtain the pre-dynamic baseline sequence. The pre-dynamic baseline sequence is recovered according to the mapping relation to obtain the dynamic baseline sequence. In addition, after the pre-dynamic baseline sequence is obtained, checking is carried out to facilitate the pre-dynamic baseline sequence to be more accurate. The pre-dynamic baseline sequence is recovered according to the mapping relation to obtain the dynamic baseline sequence.

105. displaying and printing the dynamic FHR baseline;

The obtained dynamic baseline sequence is transmitted to the displaying/printing module. The FHR baseline is drawn in a fetal monitoring drawing, displayed and printed.

Figure 2:
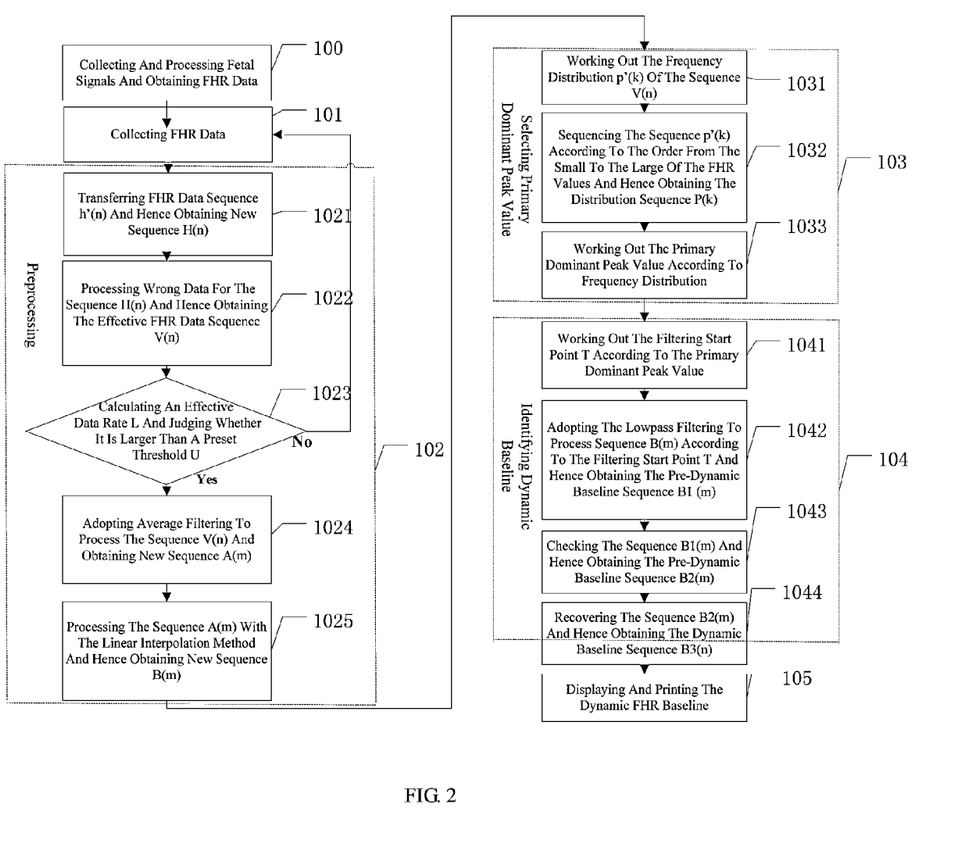
FIG. 2 is a flow chart of another embodiment of an automatically identifying FHR dynamic baseline method according to the invention.

Another embodiment of an automatically identifying FHR baseline method in the invention is described in details in the reference with the FIG. 2 in the following:

100. collecting and processing the fetal heart signals to obtain the FHR data;

The hardware filtering processing and autocorrelation algorithm are carried out with the fetal heart signals received from the ultrasonic probe in the lower computer, which calculates the FHR and uploads it to the upper computer. The processes of the upper computer comprise displaying and storing the FHR data, describing them into the FHR curve, and processing the related data, etc., wherein the hardware filtering is used for removing the frequency interference of the collected signals while the autocorrelation algorithm has characteristics of strengthening cycle signals and weakening noise, which are common techniques when the FHR is calculated.

101. collecting the FHR data within the preset duration;

The upper computer collects n-minute FHR data and obtains the FHR data sequence h'(n). FIG. 5 is original FHR data collected by the upper computer, wherein in the embodiment at least ten-minute data are needed to be collected. According to "Fetal Electronic Monitoring", generally, at least ten-minute FHR data is needed to determine the FHR baseline.

1021. transferring the FHR data sequence h'(n) and hence obtaining new sequence H(n);

Carrying out data transferring for the FHR data sequence h'(n) and hence obtaining the sequence H(n). The data obtained from the lower computer are FHR values taking bpm (beats per min) as the unit. In order to facilitate the data processing to be more accurate, the upper compute transfers the data into the FHR values taking a pulse interval (the time interval between two heartbeats; unit: ms) as the unit.

Figure 6:
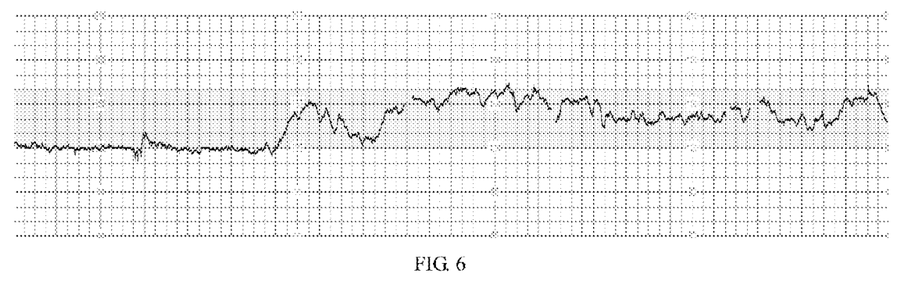
FIG. 6 is an effect diagram of FHR data after the FHR data is carried out with error data processing.

1022. processing error data for the sequence H(n) and hence obtaining the effective FHR data sequence V(n);

The invalid and error data, generated because of bad fetal heart signals in the fetal sequence, can be effectively removed according to a preset signal quality judging standard, and the remaining are effective data. FIG. 6 is a sequence of FHR data after the error data processing is carried out with FHR data.

1023. calculating an effective data rate L of a fetal heart according to the sequences V(n) and H(n) and judging whether it is larger than a preset threshold U;

The effective data rate L is judged according to the sequences V(n) and H(n). If L is larger than the preset threshold U, the next step of working out the baseline of the invention is continued to be carried out. Otherwise, the working out of the baseline is terminated, the entire flow is terminated, this section of the data is abandoned, and Step 101 is repeated to collect new FHR data.

1024. adopting average filtering to process the sequence V(n) and obtaining new sequence A(m);

The sequence V(n) is processed with an average filter (in the average filter, moving average of specific points or segmental averaging of the specific points is adopted) and obtains the sequence A(m) while establishing V→A. position mapping relation f, wherein f is a many-to-one mapping relation and describes the corresponding relation of the subscript positions of the data sequence after and before the filtering. In the embodiment, f(m) is the integral part of the result from n divided by the preset threshold.

Figure 7:
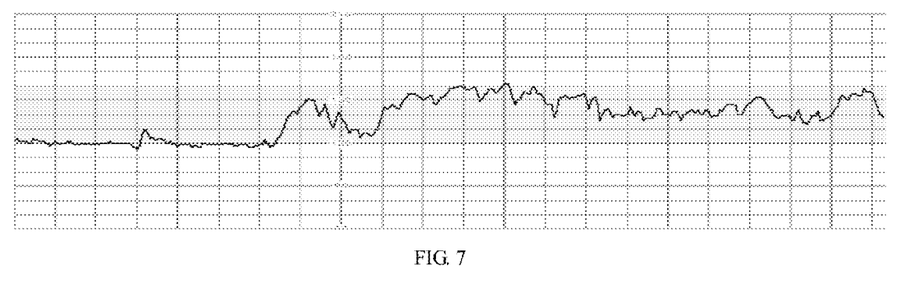
FIG. 7 is an effect diagram of FHR data after the FHR data is carried out with interpolation processing.

1025. processing the sequence A(m) with the linear interpolation method and hence obtaining new sequence B(m);

An invalid data part in the sequence A(m) is fitted with a linear interpolation method, and the sequence B(m) is obtained. The linear interpolation method is a simple interpolation method using the principle of flow free to work out other points on the straight line. FIG. 7 is a sequence of FHR data after the interpolation processing is carried out with FHR data.

The above Steps 1021, 1022, 1023, 1024 and 1025 are the steps of preprocessing the FHR data in the embodiment.

In addition, the steps of preprocessing the FHR data are not limited to the abovementioned steps. The moving average method and/or the interpolation fitting method and/or the method which is known in the industry and directly takes bpm (beats per min) as a unit to remove error data are adopted.

1031. working out the frequency distribution p'(k) of the sequence V(n).;

Each FHR frequency of the effective FHR data sequence V(n) is worked out and the frequency distribution p'(k) is obtained.

Figure 8:
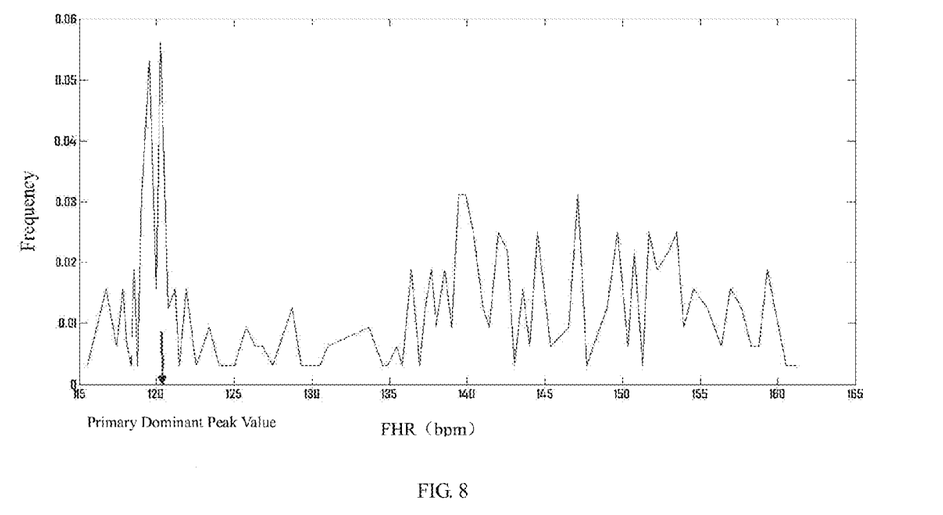
FIG. 8 is an effect diagram of the frequency distribution of FHR data and a primary dominant peak value selection.

1032. sequencing the sequence p'(k) according to the order from small to large FHR values and hence obtaining the distribution sequence P(k);

1033. working out the primary dominant peak value according to frequency distribution;

It is judged whether there is the primary dominant peak value in the sequence P(k). The primary dominant peak value is the FHR value corresponding to the frequency value in the sequence P(k) which is larger than I previous frequency values and larger than J latter frequency values. If there is not a primary dominant peak value, the FHR value corresponding to the maximum frequency is selected to be taken as the primary dominant peak value. If there is a primary dominant peak value, it is traversed. The FHR value, corresponding to the primary frequency value of which the swept area is S times larger than the total frequency distribution area, is taken as the primary dominant peak value (wherein I, J and S can be preset according to actual conditions). FIG. 8 is an effect diagram of the frequency distribution of FHR data and a primary dominant peak value selection. The value indicated by an arrow in the figure is the selected primary dominant peak value. In addition, there are many methods of selecting the primary dominant peak value. The invention is not limited to the above steps. Directly according to the maximum frequency value, according to the proportion between the frequency value in the sequence P(k) and the maximum frequency value exceeds the threshold, or according to the rule that the sum of all frequency values prior to the frequency value exceeds a preset threshold, the FHR value, corresponding to the frequency value meeting the conditions, may be taken as the primary dominant peak value.

Step 1041: working out the filtering start point T according to the primary dominant peak value;

The filtering start point T is worked out according to the primary dominant peak value. The value is selected from K previous points in the sequence B(m) and is the closest to the primary dominant peak value, wherein the distance between the value and the primary dominant peak value does not exceed the threshold Q. The value is just the filtering start point T (wherein K and Q are preset according to the actual conditions).

In addition, there are many methods of selecting the filtering start point. The invention is not limited to the above steps. In addition, the primary dominant peak value may be directly selected as the filtering start point, and the average value of all values in the sequence B(m) also may be taken as the filtering start point, wherein, the distance between all the values and the primary dominant peak value does not exceed the preset threshold.

Figure 9:
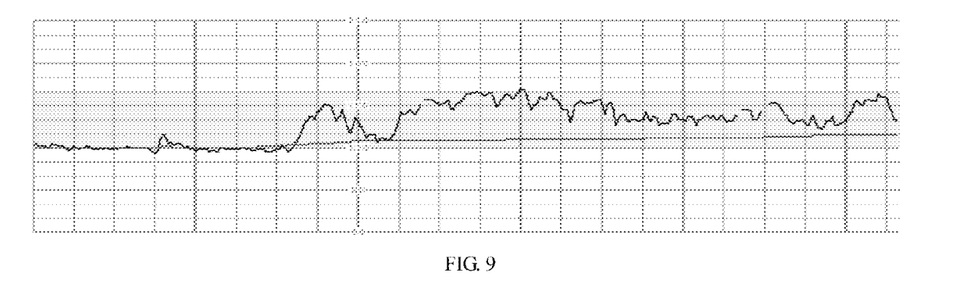
FIG. 9 is an effect diagram of FHR data after the FHR data is carried out with lowpass filtering.

1042. adopting the lowpass filtering to process sequence B(m) according to the filtering start point T and hence obtaining the pre-dynamic baseline sequence B1 (m);

The sequence B(m) and the filtering start point T are input into a lowpass filter. Compared with the FHR data, its baseline is a low-frequency signal which needs to be obtained through the lowpass filtering. Each value in the sequence B(m) is judged prior to the filtering. If the absolute difference between the value and the primary dominant peak value exceeds threshold M, the filtering is not carried out with the value. Otherwise, the value is filtered and calculated. With a two-way filtering technique, this may eliminate phase deviation. The forward direction of the sequence B(m) first passes through a lowpass filter and hence obtains the sequence B0(m). Second, the reverse direction of the sequence B0(m) passes through the lowpass filter, is further filtered and hence obtains the preset baseline sequence B1(m). The baseline curve in FIG. 9 is a pre-dynamic baseline sequence (wherein the threshold M may be preset according to actual conditions) which is first processed with the lowpass filtering. The following Step 1044 is carried out again and then may realize the automatic identification of the FHR baseline in the invention. In addition, in the embodiment, the following Step 1043 also may be added to further check and optimize the automatic identification of the FHR baseline.

Figure 10:
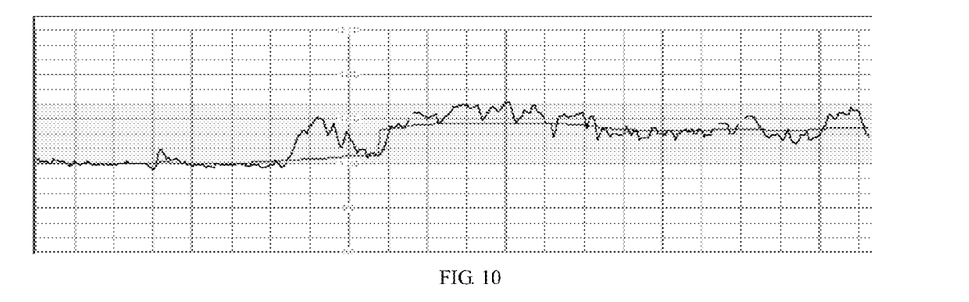
FIG. 10 is an effect diagram of FHR data after the baseline is checked.

1043. checking the sequence B1(m) and hence obtaining the pre-dynamic baseline sequence B2(m);

The sequence B1(m) and the sequence B(m) are corrected, thus obtaining the sequence C(m) and calculating number N in the sequence C(m) continuously larger than zero. If the N is larger than threshold R, the positions of N data in the sequence C(m) are marked; similarly, the positions in the sequence C(m), where the number of the positions continuously smaller than zero exceeds threshold R, are marked (wherein R may be preset according to actual conditions). The marked positions correspond to the data in the sequence B(m). The data in these positions are replaced with the sequence B(m). Meanwhile, these positions, corresponding to the positions in the sequence V(n), are worked out according to the mapping relation f. The data of the corresponding position in the sequence V(n) are replaced with the sequence V(n) in Step 103. And then Step 103 and Steps 1041 and 1042 of Step 104 are implemented again. The data on these positions in the sequence B1(m) are replaced with the obtained sequence, thus obtaining the pre-dynamic baseline sequence B2(m). If the abovementioned steps do not have marked positions, the pre-dynamic baseline sequence B2(m) is the sequence B1(m). The baseline curve in FIG. 10 is the pre-dynamic baseline sequence obtained after the checking.

Figure 11:
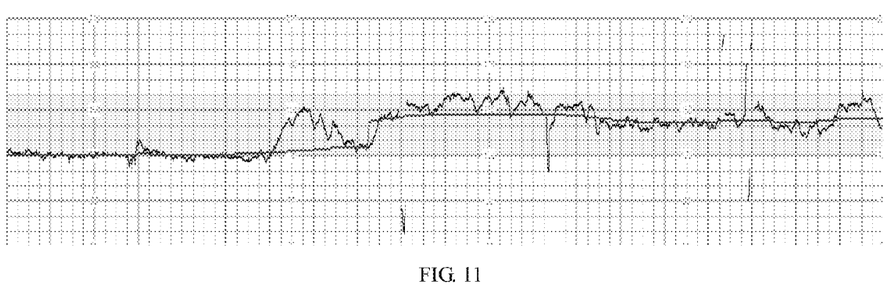
FIG. 11 is an effect diagram of a recovered dynamic baseline of FHR data.

1044. recovering the sequence B2(m) and hence obtaining the dynamic baseline sequence B3(n);

According to the mapping relation f, the data recovery is carried out for the sequence B2(m) with a copy method. Equivalently, each datum in m data is copied and overall recovered to n data, thus obtaining the dynamic baseline sequence B3(n) corresponding to the FHR sequence h'(n). The baseline curve in FIG. 11 is the dynamic baseline sequence obtained after the recovery.

105. displaying and printing the dynamic baseline;

The obtained dynamic baseline sequence B3(n) is transmitted to a displaying/printing module, the FHR baseline is drawn on the fatal monitoring drawing, and it is displayed and printed.

Figure 3:
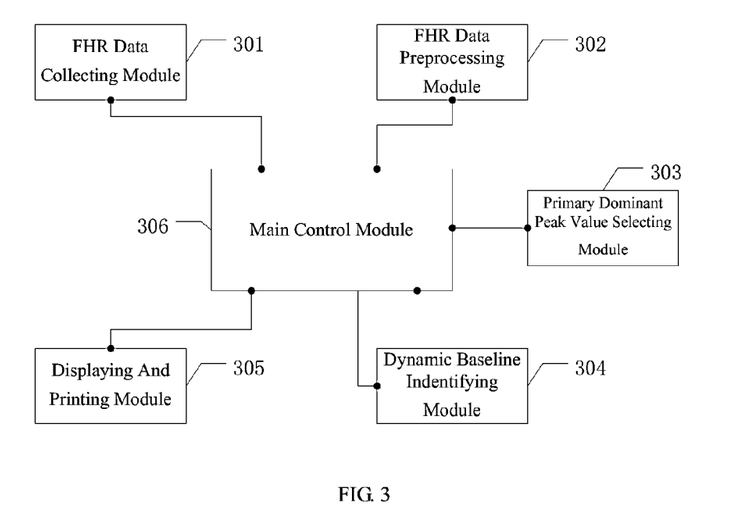
FIG. 3 is a framework block diagram of one embodiment of an automatically identifying FHR dynamic baseline apparatus according to the invention.

The invention relates to an apparatus for automatically identifying FHR baseline. As shown in FIG. 3, it mainly comprises:

an FHR data collecting module 301 connected with the main control module 306, used for collecting the FHR data within the preset duration, further obtaining FHR data sequence h'(n), and transmitting the FHR data sequence h'(n) to the main control module 306;

an FHR data preprocessing module 302 connected with the main control module 306, used for carrying out data transfer, error data processing, effective data rate comparison, average filtering and interpolation processing for the FHR data sequence h'(n) transmitted by the main control module, obtaining the preprocessed FHR data sequence B(m), and transmitting the corresponding results obtained during preprocessing to the main control module 306;

a primary dominant peak value selecting module 303 connected with the main control module 306, used for carrying out frequency transferring, distribution sequencing and primary dominant peak value judging for the corresponding results obtained during preprocessing that the main control module is transmitted, and transmitting the results to the main control module 306;

a dynamic baseline identifying module 304 connected with the main control module 306, used for working out the filtering start point T according to the preprocessed FHR data sequence B(m) and primary dominant peak value transmitted by the main control module, carrying out the lowpass filtering and data recovery for the sequence B(m) to further obtain the dynamic FHR baseline, and transmitting the results to the main control module 306;

a displaying/printing module 305 connected with the main control module 306 and used for identifying the results according to the dynamic baseline transmitted by the main control module, and displaying the FHR baseline on a fetal monitoring drawing and printing it.

the main control module 306 connected with the FHR data collecting module 301, the FHR data preprocessing module 302, the primary dominant peak value selecting module 303, the dynamic baseline identifying module 304 and the displaying/printing module 305, and used for controlling the operation of the FHR data collecting module 301, the FHR data preprocessing module 302, the primary dominant peak value selecting module 303, the dynamic baseline identifying module 304 and the displaying/printing module 305, wherein the main control module 306 in the embodiment in the invention may be a programmable microprocessor of a known structure.

Figure 4:
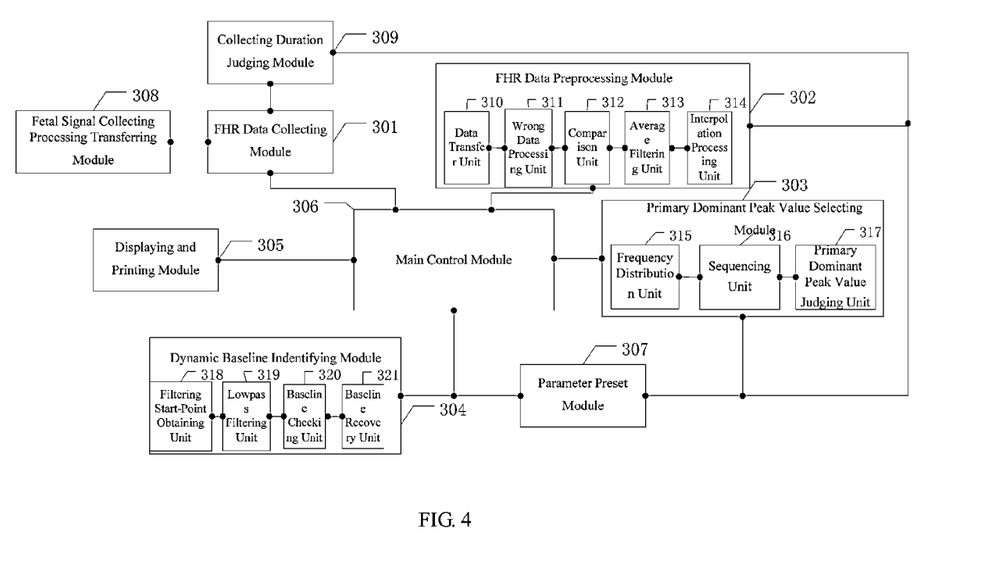
FIG. 4 is a framework block diagram of another embodiment of an automatically identifying FHR dynamic baseline apparatus according to the invention.

In order to understand the invention in more details, an apparatus for automatically identifying FHR baseline in the invention is described with another embodiment. Please see FIG. 4, the detailed description is as follows:

The invention relates to an apparatus for automatically identifying FHR baseline, also comprising:

a fetal heart signal collecting processing transferring module 308 connected with the FHR data collecting module 301, being an ultrasonic probe device collecting, processing and transferring signals, and used for collecting the fetal heart signals received by the ultrasonic probe and transferring the signals into the FHR data, wherein hardware filtering processing and autocorrelation algorithm are carried out with the collected fetal heart signals in the embodiment, calculates the FHR and transmits them to the FHR data collecting module 301;

the collecting duration judging module 309 connected with the FHR data collecting module and used for judging whether the collecting time exceeds the preset duration, wherein if the collecting time exceeds the preset duration, timeout signals are transmitted to the FHR data collecting module 301; and a parameter preset module 307 connected with the collecting duration judging module 309, the FHR data preprocessing module 302, the primary dominant peak value selecting module 303 and the dynamic baseline identifying module 304, and used for presetting the parameters of each module.

The FHR data preprocessing module 302 further comprises:

a data transfer unit 310 used for transferring the FHR data sequence h'(n) collected by the FHR data collecting module and obtaining new FHR value sequence H(n) taking a pulse interval as a unit;

an error data processing unit 311 used for carrying out the error data processing for the FHR value sequence H(n) according to a preset signal quality judging standard and obtaining an effective FHR data sequence V(n);

a comparison unit 312 used for calculating an effective data rate L of the fetal heart according to the sequences V(n) and H(n) and judging whether it is larger than a preset threshold U, wherein if L is larger than the preset threshold U, the data continue to be preprocessed; otherwise, the data stop being preprocessed and new FHR data are collected again;

an average filtering unit 313 used for carrying out the average filtering processing for the effective FHR data sequence V(n) and hence obtaining the sequence A(m) while establishing a position mapping relation f of the two sequences V(n) and A(m); and an interpolation processing unit 314 used for fitting an invalid data part in the sequence A(m) with a linear interpolation method and hence obtaining the sequence B(m).

The primary dominant peak value selecting module 303 further comprises:

a frequency distribution unit used for working out each FHR frequency of the effective FHR data sequence V(n) and hence obtaining a frequency distribution sequence p'(k);

a sequencing unit used for sequencing the sequence p'(k) according to the order from small to large of the FHR values and hence obtaining the distribution sequence P(k);

a primary dominant peak value judging unit used for judging whether there is a frequency value in the sequence P(k) larger than I previous frequency values and larger than J latter frequency values, wherein if there is such a frequency value, the FHR value corresponding the frequency value is taken as the dominant peak value; If there is no primary dominant peak value, the FHR value corresponding to the maximum frequency is selected as the primary dominant peak value, wherein if there is the primary dominant peak value, it is traversed. The FHR value, corresponding to the primary frequency value of which the swept area is S times larger than the total frequency distribution area, is taken as the primary dominant peak value, wherein I, J and S are preset parameters.

The dynamic baseline identifying module 304 further comprises:

a filtering start-point obtaining unit 318 used for working out the filtering start point T according to the primary dominant peak value, and selecting the value in K previous points in the sequence B(m), wherein the distance between the value and the primary dominant peak value does not exceed threshold Q; and the value is the closest to the primary dominant peak value; the value is just the filtering start point T, wherein K and Q are preset parameters;

a lowpass filtering unit 319 used for processing the sequence B(m) with the lowpass filtering according to the filtering start point T and hence obtaining a pre-dynamic baseline sequence B1(m);

a baseline checking unit 320 used for checking the pre-dynamic baseline sequence B1(m) obtained through the lowpass filtering unit and hence obtaining the pre-dynamic baseline sequence B2(m), wherein the pre-dynamic baseline sequence B2(m) obtains the dynamic baseline sequence through the baseline recovery unit; and the baseline recovery unit 321 used for carrying out the data recovery for the pre-dynamic baseline sequence with a copy method according to the mapping relation f and hence obtaining a dynamic baseline sequence B3(n).

The above are only preferable embodiments of the invention and do not limit the invention. Any modification, equal replacement and improvement implemented within the spirit and principle of the invention shall fall within the protection scope of the invention.

The invention claimed is:

1. An automatically identifying Fetal Heart Rate (FHR) baseline apparatus, comprising a FHR data collecting module; a FHR data preprocessing module; a primary dominant peak value selecting module; a dynamic baseline identifying module and a main control module;

wherein the FHR data collecting module is connected with the main control module, is configured for collecting the FHR data within a preset duration, further obtains FHR data sequence h'(n), and transmits the FHR data sequence h'(n) to the main control module;

wherein the FHR data preprocessing module is connected with the main control module, is configured for preprocessing the FHR data sequence h'(n) transmitted by the main control module, obtains the preprocessed FHR data sequence B(m), and transmits the corresponding results obtained during preprocessing to the main control module; wherein the primary dominant peak value selecting module is connected with the main control module, is configured for selecting the primary dominant peak value according to the frequency distribution of the corresponding results obtained during preprocessing that the main control module is transmitted, and transmits the results to the main control module;

wherein the dynamic baseline identifying module is connected with the main control module, is configured for working out the filtering start point T according to the primary dominant peak value transmitted by the main control module, carries out low pass filtering and data recovery for the preprocessed FHR data sequence B(m) to further obtain the dynamic FHR baseline, and transmits the results to the main control module; and wherein the main control module is connected with the FHR data collecting module, the FHR data preprocessing module, the primary dominant peak value selecting module, the dynamic baseline identifying module and a displaying/printing module, and configured for controlling the operation of the FHR data collecting module, the FHR data preprocessing module, the primary dominant peak value selecting module and the dynamic baseline identifying module.

2. The automatically identifying FHR baseline apparatus according to claim 1, further comprising a fetal heart signal collecting, processing, and transferring module, a collecting duration judging module, a parameter preset module and the displaying/printing module, wherein the fetal heart signal collecting, processing, and transferring module is connected with the FHR data collecting module and configured for collecting the fetal heart signals received from an ultrasonic probe, transferring the signals into the FHR data and transmitting the signals to the FHR data collecting module, the collecting duration judging module is connected with the FHR data collecting module and configured for judging whether the collecting time exceeds the preset duration; and if the collecting time exceeds the preset duration, transmitting timeout signals to the FHR data collecting module, the parameter preset module is connected with the collecting duration judging module, the FHR data preprocessing module, the primary dominant peak value selecting module and the dynamic baseline identifying module, and configured for presetting the parameters of each module, and the displaying/printing module is connected with the main control module and configured for identifying the results according to the dynamic baseline transmitted by the main control module, displaying the FHR baseline on a fetal monitoring drawing and printing the FHR baseline.

3. The automatically identifying FHR baseline apparatus according to claim 1, further comprising:

a data transfer unit configured for transferring the FHR data sequence h'(n) collected by the FHR data collecting module and hence obtaining new FHR value sequence H(n) taking a pulse interval as a unit; an error data processing unit configured for carrying out the error data processing for the FHR value sequence H(n) according to a preset signal quality judging standard and hence obtaining an effective FHR data sequence V(n); a comparing unit configured for calculating an effective data rate L of a fetal heart according to the sequences V(n) and H(n) and judging whether it is larger than a preset threshold U, wherein if L is larger than the preset threshold U, the data continue to be preprocessed and otherwise the data stops being preprocessed and new FHR data are collected again;

an average filtering unit configured for carrying out the average filtering processing for the effective FHR data sequence V(n) and hence obtaining the sequence A(m) while establishes a position mapping relation f of the two sequences V(n) and A(m); and an interpolation processing unit configured for fitting an invalid data part in the sequence A(m) with a linear interpolation method and hence obtaining a sequence B(m).

4. The automatically identifying FHR baseline apparatus according to claim 3, wherein the primary dominant peak value selecting module further comprises:

a frequency distribution unit for working out each FHR frequency of the effective FHR data sequence V(n) and hence obtaining a frequency distribution sequence p'(k);

a sequencing unit configured for sequencing the sequence p'(k) from small to large FHR values and hence obtaining a distribution sequence P(k);

a primary dominant peak value judging unit configured for judging whether there is a frequency value in the sequence P(k) larger than I previous frequency values and larger than J latter frequency values, wherein if there is the frequency value, the FHR value corresponding the frequency value is taken as a primary dominant peak value, and if there is not such a frequency value, the FHR value corresponding to the maximum frequency is selected as the primary dominant peak value, if there is the primary dominant peak value, it is traversed; the FHR value, corresponding to the primary frequency value of which the swept area is S times larger than the total frequency distribution area, is taken as the primary dominant peak value, Wherein I, J and S are preset parameters.

5. The automatically identifying FHR baseline apparatus according to claim 4, wherein the dynamic baseline identifying module further comprises:

a filtering start-point obtaining unit configured for working out the filtering start point T according to the primary dominant peak value, and selecting the value in K previous points in the sequence B(m), wherein the distance between the value and the primary dominant peak value does not exceed threshold Q and the value is the closest to the primary dominant peak value, wherein the value is the filtering start point T, and K and Q are preset parameters; a low pass filtering unit configured for processing the sequence B(m) with low pass filtering according to the filtering start point T and hence obtaining a pre-dynamic baseline sequence B1(m); and a baseline recovery unit configured for carrying out the data recovery for the pre-dynamic baseline sequence with a copy method according to the mapping relation f and hence obtaining a dynamic baseline sequence B3(n).

6. The automatically identifying FHR baseline apparatus according to claim 5, wherein the dynamic baseline identifying module further comprises:

a baseline checking unit configured for checking the pre-dynamic baseline sequence B1(m) obtained through the low pass filtering unit and hence obtaining the pre-dynamic baseline sequence B2(m), wherein the pre-dynamic baseline sequence B2(m) obtains the dynamic baseline sequence through the baseline recovery unit.

7. An automatically identifying Fetal Heart Rate (FHR) baseline method, comprising:

collecting FHR data within a preset duration to obtain an FHR data sequence h'(n);

preprocessing the collected FHR data sequence h'(n) to obtain a corresponding FHR data sequence;

selecting a primary dominant peak value according to the frequency distribution of the corresponding FHR data sequence; and working out a filtering start point according to the primary dominant peak value, carrying out low pass filtering and data recovery for the corresponding FHR data sequence according to the filtering start point, and further obtaining a dynamic FHR baseline, wherein the method further comprises collecting fetal heart signals received from an ultrasonic probe and transferring the fetal heart signals into the FHR data and further comprises displaying and printing the dynamic FHR baseline.

8. The automatically identifying FHR baseline method according to claim 7, wherein preprocessing the collected FHR data sequence comprises:

transferring the FHR data sequence h'(n) and obtaining new FHR value sequence H(n) taking a pulse interval as a unit;

carrying out error data processing for the FHR value sequence H(n) according to a preset signal quality judging standard and obtaining an effective FHR data sequence V(n);

calculating an effective data rate L of a fetal heart according to the sequences V(n) and H(n) and judging whether it is larger than a preset threshold U, wherein if L is larger than the preset threshold U, the data preprocessing continues and otherwise the data preprocessing stops and new FHR data is collected;

when the L is larger than the preset threshold U, the average filtering processing the effective FHR data sequence V(n) to obtain the sequence A(m) while establishing a position mapping relation f of the two sequences V(n) and A(m); and fitting an invalid data part in the sequence A(m) with a linear interpolation method and hence obtaining a sequence B(m).

9. The automatically identifying FHR baseline method according to claim 8, wherein selecting a primary dominant peak value comprises:

working out each FHR frequency for the corresponding FHR data sequence (i.e. the effective FHR data sequence V(n)) during preprocessing to obtain frequency distribution p'(k);

sequencing the sequence p'(k) from small to large FHR values and hence obtaining the distribution sequence P(k);

judging whether there is a frequency value in the sequence P(k) larger than I previous frequency values and larger than J latter frequency values, wherein if there is the frequency value, the FHR value corresponding to the frequency value is taken as the primary dominant peak value and if there is not, the FHR value corresponding to the maximum frequency is selected to be taken as the primary dominant peak value; if there is the primary dominant peak value, it is traversed; the FHR value, corresponding to the primary frequency value of which the swept area is S times larger than the total frequency distribution area, is taken as the primary dominant peak value, wherein I, J and S are preset parameters.

10. The automatically identifying FHR baseline method according to claim 9, wherein working out a filtering start point comprises:

working out the filtering start point T according to the primary dominant peak value, and selecting the value from K previous points in the sequence B(m), wherein the distance between the value and the primary dominant peak value does not exceed threshold Q and the value is the closest to the primary dominant peak value, wherein the value is the filtering start point T, and K and Q are preset parameters;

carrying out low pass filtering for the sequence B(m) and the filtering start point T and judging each value in the sequence B(m) before the filtering, wherein If the absolute difference between the value and the primary dominant peak value exceeds threshold M, the filtering is not carried out on the value, and otherwise the low pass filtering is carried out to obtain the pre-dynamic baseline sequence B1(m), wherein M is a preset parameter; and carrying out data recovery for the pre-dynamic baseline sequence with a copy method according to the mapping relation f and hence obtaining a dynamic baseline sequence B3(n).

11. The automatically identifying FHR baseline method according to claim 10, wherein carrying out low pass filtering further comprises: firstly, passing a forward direction of the sequence B(m) through a low pass filter and hence obtaining sequence B0(m), and secondly, passing the reverse direction of the sequence B0(m) through the low pass filter and hence obtaining the preset baseline sequence B1(m).

12. The automatically identifying FHR baseline method according to claim 10, wherein the method further comprises:

checking the sequence B1(m), correcting the sequence B1(m) and B(m) to obtain the sequence C(m), and calculating number N continuously larger than zero in the sequence C(m), wherein if the N is larger than threshold R, the positions of N data in the sequence C(m) are marked and similarly, the positions in the sequence C(m), where the number continuously smaller than zero exceeds the threshold R, are marked, the marked positions corresponding to the data in the sequence B(m), the data on the positions are replaced with the sequence B(m), meanwhile, these positions, corresponding to the positions in the sequence V(n), are worked out according to the mapping relation f, the data of the corresponding positions in the sequence V(n) are replaced with the sequence V(n) in selecting a primary dominant peak value, and then selecting a primary dominant peak value and working out the filtering start point T and carrying out the low-pass filtering are implemented again, the data on these positions in the sequence B1(m) are replaced with the obtained sequence, thus obtaining the pre-dynamic baseline sequence B2(m) and if the above-mentioned steps do not result in marked positions, the pre-dynamic baseline sequence B2(m) is the sequence B1(m), wherein R is a preset parameter.

* * * * *